United States Patent [19]

Brinon

[11] Patent Number: 5,611,778
[45] Date of Patent: Mar. 18, 1997

[54] SURGICAL INSTRUMENT FOR PERFORMING EPIDURAL ANESTHESIA

[75] Inventor: Thierry Brinon, Montsoult, France

[73] Assignee: Vygon, Ecouen, France

[21] Appl. No.: 331,646

[22] PCT Filed: May 12, 1993

[86] PCT No.: PCT/FR93/00465

§ 371 Date: Nov. 10, 1994

§ 102(e) Date: Nov. 10, 1994

[87] PCT Pub. No.: WO93/23109

PCT Pub. Date: Nov. 25, 1993

[30] Foreign Application Priority Data

May 14, 1992 [FR] France .................. 92 05857

[51] Int. Cl.$^6$ ........................... A61M 5/00
[52] U.S. Cl. ........................... 604/117; 604/158
[58] Field of Search ........................... 604/117, 158, 604/161, 164, 178, 280, 282

[56] References Cited

U.S. PATENT DOCUMENTS

| 2,198,666 | 4/1940 | Gruskin .................. 604/117 |
| 2,388,800 | 1/1944 | Burke .................. 604/117 |
| 3,750,667 | 8/1973 | Pshenichny et al. .................. 604/117 |
| 4,500,313 | 2/1985 | Young . | |
| 4,645,491 | 2/1987 | Evans .................. 604/158 |
| 5,084,022 | 1/1992 | Claude . | |
| 5,106,376 | 4/1992 | Mononen et al. .................. 604/158 X |
| 5,129,889 | 7/1992 | Hahn et al. .................. 604/158 X |
| 5,292,309 | 3/1994 | Van Tassel et al. .................. 604/117 |
| 5,320,608 | 6/1994 | Gerrone .................. 604/117 |
| 5,353,787 | 10/1994 | Price .................. 604/117 X |
| 5,391,159 | 2/1995 | Hirsch et al. .................. 604/178 X |

FOREIGN PATENT DOCUMENTS

| 0406586 | 1/1991 | European Pat. Off. . | |
| 288589 | 5/1953 | Switzerland . | |
| 9010466 | 9/1990 | WIPO . | |
| WO91/05577 | 5/1991 | WIPO .................. 604/117 |

Primary Examiner—Sam Rimell
Attorney, Agent, or Firm—Mason, Kolehmainen, Rathburn & Wyss

[57] ABSTRACT

Surgical instrument for epidural anesthesia comprising a needle and catheter associated therewith which slides in the needle. The catheter has a set of main axial reference marks coinciding with an index on the needle. A reading will indicate the length of the catheter extending from the distal end of the needle. The catheter also includes a set of auxiliary reference marks distinguishable from the main reference marks.

8 Claims, 4 Drawing Sheets

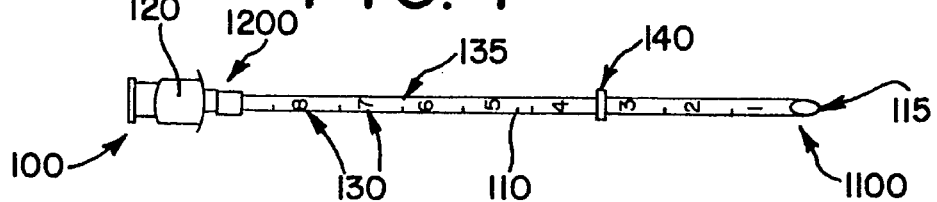
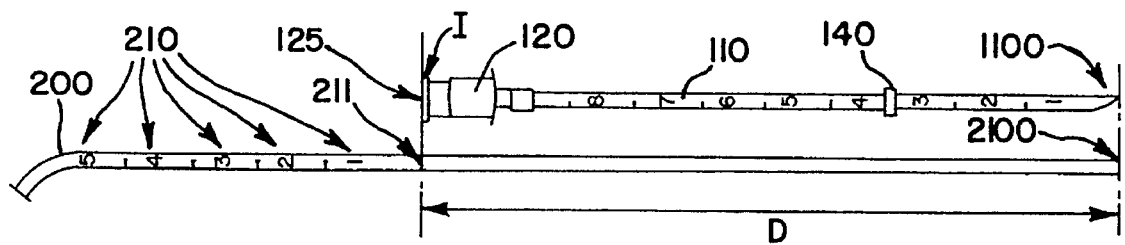
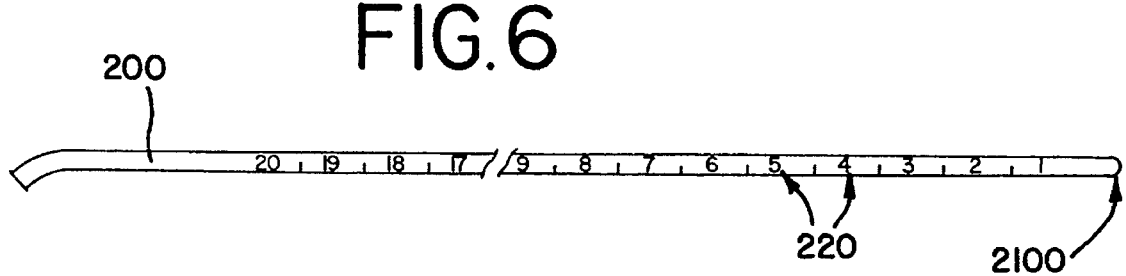

SURGICAL INSTRUMENT FOR PERFORMING EPIDURAL ANESTHESIA

The present invention relates to the field of surgical instruments comprising a needle and an associated catheter capable of sliding inside the needle, in particular for performing epidural anesthesia.

Epidural anesthesia is a technique that is widespread at present, and as shown in FIG. 1 it consists in putting a catheter C into place in the epidural space P of a patient in order to inject an anesthetic by means of a needle A which is provided at its distal end 5 with a tapering chamfer tip, also known as a Tuohy needle.

To perform epidural anesthesia, the anesthetist generally begins by inserting the needle A in the back of the patient until the distal end 5 of the needle penetrates into the epidural space P, then the catheter C is inserted via the proximal opening 10 of the needle until it penetrates into the epidural space P via the distal end 5 of the needle.

In order to avoid trauma to this sensitive region of the patient, it is important to avoid pushing the needle in too deep, and thus to know the length of needle that has been inserted into the back of the patient. To do this, a Tuohy needle A of the prior art is generally provided, as shown in FIG. 2, with marks 15 that are spaced apart axially uniformly along its length, thereby enabling the anesthetist to deduce by calculating the length of needle that has been inserted into the back of the patient, i.e. by knowing the total number of marks on the needle and by subtracting therefrom the number of marks that remain visible after the needle has been inserted.

It is also important to know the length of catheter that has been inserted into the epidural space, and the catheter C is generally provided for this purpose with identical marks uniformly spaced axially along its length. To discover the length of catheter extending in the epidural space P, the anesthetist generally counts the number of marks on the catheter C that go in through the proximal opening 10 of the needle as the catheter is being pushed into the needle and after it has left the chamfer thereof, which the anesthetist can feel easily since it becomes more difficult to urge the catheter into the needle once the end of the catheter has gone beyond the distal end of the needle. Thereafter, the Tuohy needle A is withdrawn while the catheter is left in place in the epidural space in order to inject an anesthetic solution therein.

The anesthetist encounters several difficulties that occur during the various steps of performing epidural anesthesia as described above.

Firstly, to know the lengths of needle and of catheter inserted into the back of the patient, the surgeon must note or remember the total numbers of graduations carried by the needle and by the catheter, and must subtract therefrom the numbers of graduations that remain visible after insertion of the needle or of the catheter, and this is not easily done in the context of a surgical operation.

Also, when the needle is being extracted, the catheter tends to be entrained with the needle because of friction, and it then becomes difficult to establish with accuracy the length of catheter that remains in the epidural space after the needle has been withdrawn, which problem is illustrated diagrammatically in FIG. 3.

Finally, since the catheter may remain in place for several hours, there is a danger of it moving during this period and it is important to know its position accurately before any further injection of anesthetic.

The present invention provides a surgical instrument comprising a needle and an associated catheter suitable for sliding inside a needle, in particular for performing epidural anesthesia, remedying the main difficulties described above.

This surgical instrument is characterized in that the catheter is provided with a set of main axial marks suitable, when the catheter is inserted in the needle, for coinciding with an index mark defined on the needle, to indicate merely by reading and without performing any calculation, the length of catheter extending beyond the distal end of the needle, and is provided with a set of auxiliary marks easily distinguished from the main marks and suitable for indicating, merely by being read and without performing any calculations, the length of the catheter that extends from its distal end to each of said auxiliary marks.

The present invention also provides a needle and a catheter taken separately and suitable for use in forming a surgical instrument of the invention.

Other characteristics and advantages of the invention appear on reading the following detailed description of a non-limiting embodiment of the present invention and on examining the accompanying drawings, in which:

FIG. 1, described above, shows the insertion of a catheter into the epidural space of a patient;

FIG. 2 shows a needle provided with marks that are uniformly spaced apart axially, as described above and illustrating the state of the art;

FIG. 3, described above, illustrates the problems posed in the prior art by withdrawing the needle from the back of the patient while leaving the catheter in place in the epidural space;

FIG. 4 is a front view of a needle of the invention;

FIG. 5 is a side view in the plane of the front view of FIG. 4, showing a needle of the invention together with its associated catheter, likewise of the invention;

FIG. 6 is a bottom view of the catheter shown in FIG. 5;

Figure 1:
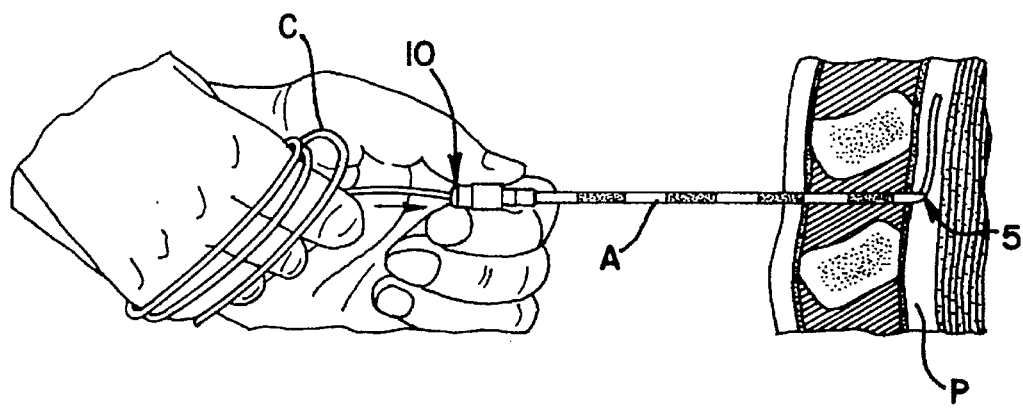
FIGS. 1 to 3 are described above to illustrate the state of the art.
Figure 2:
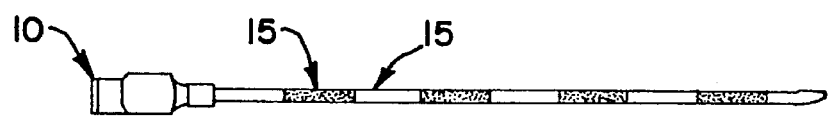
Figure 3:
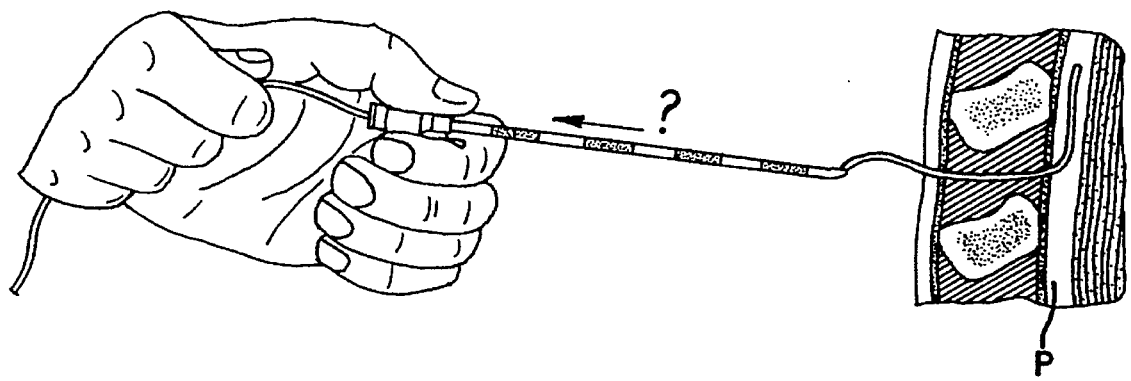

FIG. 4 shows a needle of the invention given overall reference 100, and comprising a hollow needle body 110 suitable for being inserted via its distal end 1100 into the back of a patient, and provided at its opposite end 1200 with a coupling endpiece 120. As shown, the distal end 1100 is preferably tapered in order to form a chamfer 115.

In accordance with an advantageous characteristic of the invention, the needle 100 is provided on its body 110 with graduations 130 that are axially distributed therealong, and suitable for showing directly, merely by being read and without performing any calculations, the length of the needle extending from the distal end 1100 to each of said graduations 130.

Preferably, and as shown, these graduations 130 comprise Arabic numerals printed or engraved at one centimeter intervals from the distal end 1100, together with spots 135, each placed halfway between said graduations 130.

In accordance with another advantageous characteristic of the invention, a cursor 140 is provided that is slidably mounted on the body 110 of the needle, and that is suitable for bearing against an incision made in the body of the patient and through which the needle is inserted, so as to move along the body 110 of the needle through a distance corresponding to the length of needle that has been inserted into the said incision, in a manner that is described in greater detail below.

FIG. 5 shows a surgical instrument of the present invention comprising a needle 100 as described above with reference to FIG. 4 and an associated catheter given reference 200, which catheter is suitable for sliding inside the body 110 and the endpiece 120, and is suitable for being inserted via an opening 125 provided in the coupling endpiece 120.

In accordance with a characteristic of the invention, the catheter 200 is provided with a set of main axial marks referenced 210 suitable, when the catheter 200 is inserted in the needle 100, for coinciding with an index mark I that is defined on the needle to indicate, merely by reading and without performing any calculations, the length of catheter that extends from the distal end 110 of the needle.

The index mark I can be positioned at various locations along the needle 100 without going beyond the ambit of the present invention. The plane of the opening 120 in the coupling endpiece preferably serves as the index mark I, however, it would naturally be possible to provide a window in the body 110 of the needle 100, optionally fitted with a magnifying glass or other device suitable for making it easier to read the marks on the catheter.

Preferably, in accordance with an advantageous characteristic of the invention, this set of main axial marks 210 comprises regularly spaced-apart main graduations extending from an origin 211 situated at a distance D from the distal end 2100 of the catheter, where the distance D corresponds to the distance between the distal end 1100 of the needle 100 and the index I defined thereon. As shown in FIG. 5, these main graduations are spaced apart at one centimeter intervals and they preferably comprise Arabic numerals placed by etching or printing once every centimeter from the origin 211, and separated by lines or spots located halfway between them.

The catheter 200 is provided with a set of auxiliary axial marks 220 that are easily distinguished from the main marks 210 and that are suitable for indicating, merely by being read and without performing any calculations, the length of the catheter extending from its distal end 2100 to each of said auxiliary marks 220, as shown in FIG. 6. Preferably, this set of auxiliary marks 220 comprises regularly spaced-apart auxiliary graduations extending from an origin that coincides with the distal end 2100 of the catheter. Also preferably, these auxiliary graduations 220 are Arabic numerals spaced apart at one centimeter intervals and separated by lines or points placed halfway between two numerals. The main marks and the auxiliary marks are advantageously disposed on the catheter to form two scales in the vicinity of each other so as to facilitate reading thereof. In a variant, the main marks and the auxiliary marks may be disposed on diametrically opposite faces of the catheter 200. The main marks 210 and the auxiliary marks 220 are advantageously of different colors.

The various steps of using a surgical instrument of the present invention are described with reference to FIGS. 7 to 11.

Figure 7:
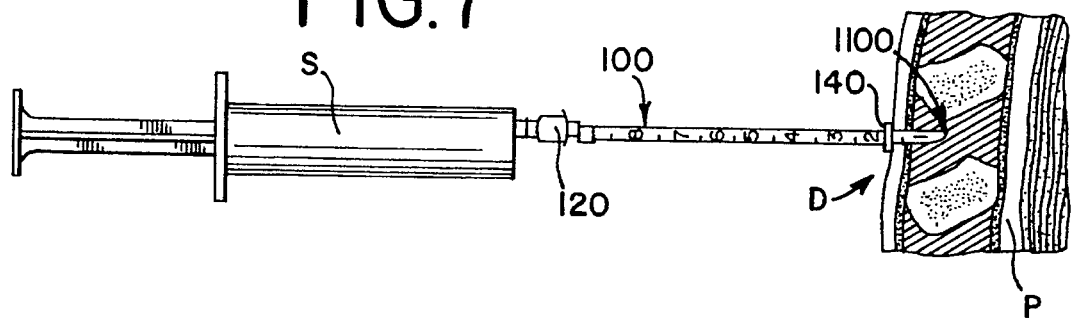
FIGS. 7 to 11 show various steps in the performance of epidural anesthesia using a surgical instrument of the invention.
Figure 8:
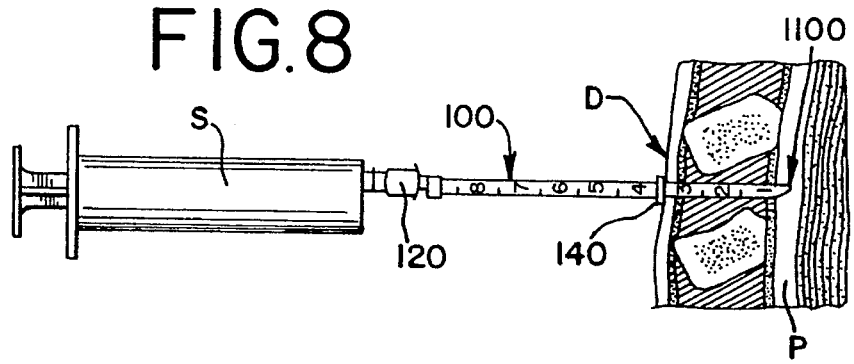

The space between the spinous processes is initially anesthetized using techniques that are known per se, then the needle 100 fitted with its sliding cursor 140 prepositioned at the distal end 1100 is inserted into the back D of the patient, the needle 100 also being connected in sealed manner via the endpiece 120 to a syringe S to constitute what is known to the person skilled in the art as a gas or a liquid mandrel, depending on whether the syringe S is filled with a gas or with a liquid. This gas or liquid mandrel technique enables the anesthetist to tell accurately when the distal end 1100 of the needle penetrates into the epidural space P. Usually, the anesthetist uses one hand to push the needle 100 towards the epidural space P, while using the other hand to keep the gas or liquid mandrel compressed until it collapses, where collapse takes place when the needle 100 penetrates into the epidural space P, as shown in FIGS. 7 and 8. It will also be seen from these figures that the cursor 140 is placed on the needle 100 at a distance $L_0$ corresponding to the length of needle inserted into the body of the patient.

Figure 9:
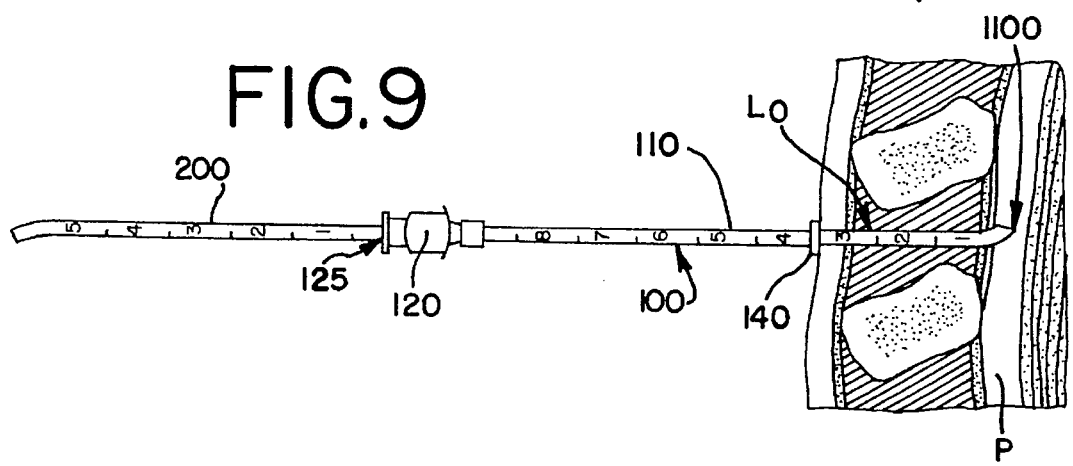

Thereafter, as shown in FIG. 9, the syringe S is disconnected, and the catheter 200 is inserted in the needle via the opening 125 of the endpiece 120 which also serves as the index mark I.

The catheter is pushed along the needle until it reaches the distal end 1100.

Figure 10:
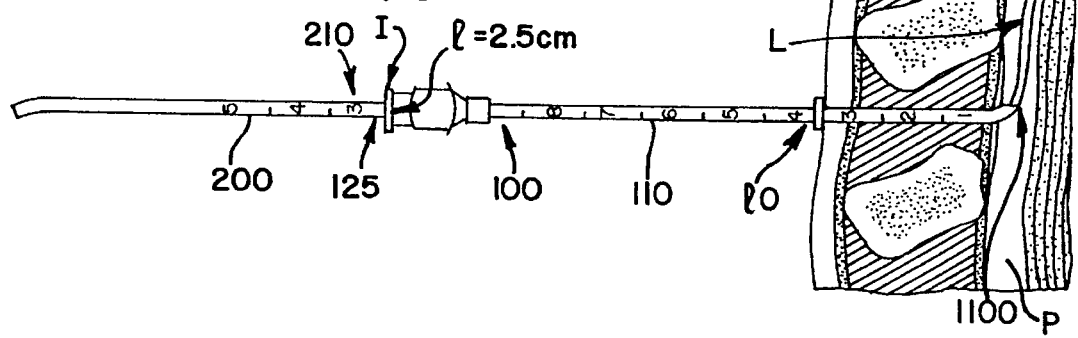

The anesthetist can then at any moment, and without performing any calculations, observe the length L of catheter that has been inserted into the epidural space P by reading the value $\pm b\ 1$ of the main graduation 210 of the catheter that coincides substantially within the index 125, as illustrated in FIG. 10.

In the example FIG. 10, it can be seen that L=2.5 cm since the index I lies between the graduations 2 and 3.

Figure 11:
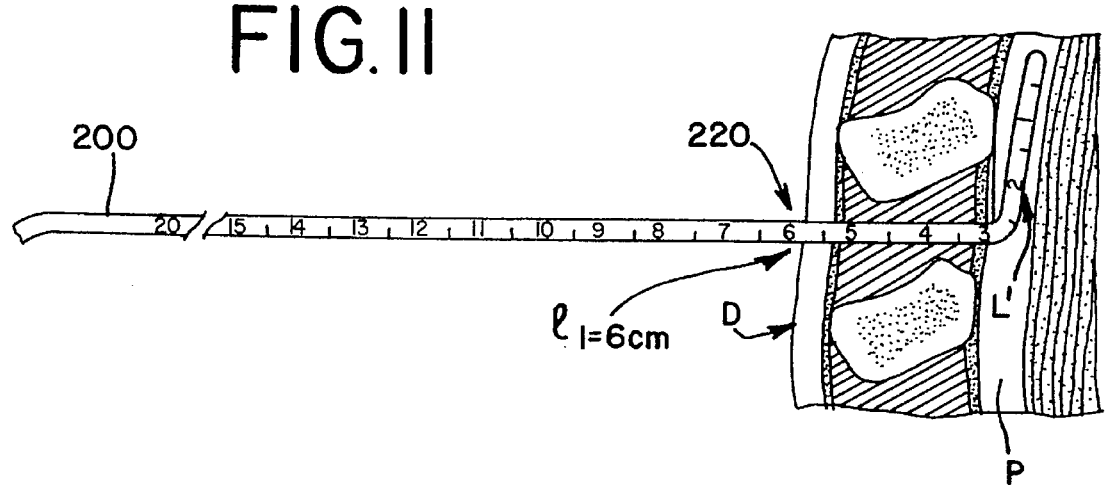
Figure 12:
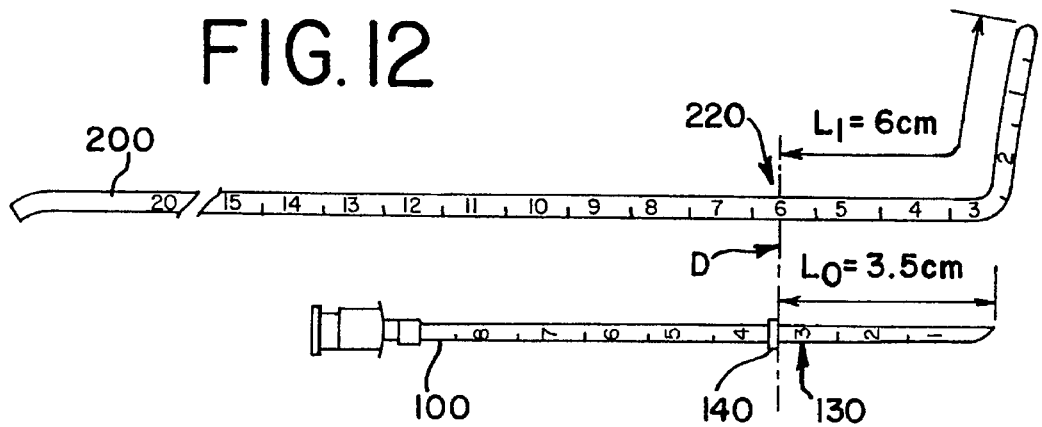
FIG. 12 shows how the length of catheter opening out into the epidural space is calculated after the needle has been withdrawn.

After the needle 100 has been withdrawn and merely by reading the auxiliary marks 220 on the catheter 200, the surgeon can discover without performing any calculations the length $L_1$ of the catheter that extends inside the body of the patient, and can easily deduce therefrom the length L' of the catheter 200 extending inside the epidural space P by subtracting the length $L_0$ given by the value $l_0$ of the graduation 130 of the needle 100 indicated by the cursor 140 from the length $L_1$ given by the value $l_1$ of the auxiliary graduation 220 closest of the body of the patient, as shown in FIGS. 11 and 12. In the example of FIGS. 10, 11, and 12, the needle has been withdrawn without entraining the catheter out from the epidural space since L=2.5 cm and $L'=L_1-L_0=6-3.5=2.5$ cm=L.

Finally, a surgical instrument of the invention is particularly simple and rapid in use and may be applied, without going beyond the ambit of the invention, to surgical operations other than epidural anesthesia, e.g. other local or regional anesthesias.

I claim:

1. A surgical instrument for performing epidural anesthesia comprising:

a needle having an index mark defined thereon; and an associated catheter sliding inside said needle, said catheter having a set of main axial marks that when said catheter is inserted in said needle, coincide with said index mark on said needle, to indicate merely by reading and without performing any calculations, the length of said catheter extending beyond the distal end of said needle, said catheter further having a set of auxiliary marks easily distinguished from said main marks that are suitabe for indicating, merely by being read and without performing any calculations, the length of said catheter that extends from its distal end to each of said auxiliary marks; and a cursor that is slidably mounted on said needle, said cursor bearing against the edge of an incision through which said needle is inserted and moving along said needle through a distance corresponding to the length that said needle is inserted into said incision.

2. A surgical instrument according to claim 1, wherein said set of main axial marks comprises regularly spaced-apart main graduations extending from an origin situated at a distance from the distal end of said catheter, said distance corresponding to the distance between the distal end of said needle and said index mark defined thereon.

3. A surgical instrument according to claim 2, wherein said main graduations are spaced apart at one centimeter intervals.

4. A surgical instrument according to claim 1, wherein said set of auxiliary marks comprises regularly spaced-apart auxiliary graduations extending from an origin that coincides with the distal end of said catheter.

5. A surgical instrument according to claim 4, wherein said auxiliary graduations are spaced apart at one centimeter intervals.

6. A surgical instrument according to claim 1, wherein said main axial marks and said auxiliary marks are disposed on the catheter to form two scales in the vicinity of each other that facilitates the reading thereof.

7. A surgical instrument for performing epidural anesthesia comprising:

a needle having an index mark defined thereon; and an associated catheter sliding inside said needle, said catheter having a set of main axial marks that when said catheter is inserted in said needle, coincide with said index mark on said needle, to indicate merely by reading and without performing any calculations, the length of said catheter extending beyond the distal end of said needle, said catheter further having a set of auxiliary marks easily distinguished from said main marks that are suitable for indicating, merely by being read and without performing any calculations, the length of said catheter that extends from its distal end to each of said auxiliary marks, wherein said main axial marks and said auxiliary marks are of different colors.

8. A process of performing epidural anesthesia utilizing a needle that has axially spaced-apart graduations suitable for indicating directly, merely by reading and without performing any calculations, the length of said needle extending from its distal end to each of said graduations; that is adapted to receive a catheter suitable for sliding inside said needle, said catheter being provided with axial marks comprising regularly spaced-apart graduations extending from an origin that coincides with the distal end of said catheter and suitable for indicating, merely by being read and without performing any calculations, the length of the catheter that extends from its distal end to each of said marks; and that is provided with a cursor that is slidably mounted on said needle so as to bear against the edge of an incision through which said needle is to be inserted, comprising the following steps:

a) inserting into a patient said needle until said needle penetrates into the epidural space, said cursor moving along said needle through a distance corresponding to the length of said needle inserted into said incision, said cursor being prepositioned at the distal end of said needle;

b) inserting said catheter into said needle and pushing said catheter into the epidural space;

c) withdrawing said needle; and d) subtracting the length given by the value of the graduation of the needle indicated by said cursor from the length given by the value of the graduation of the catheter closest of the body of the patient, in order to determine the length of the catheter extending inside the epidural space so as to insure that said catheter is correctly positioned within said epidural space before anesthetic is injected using said catheter.

* * * * *

UNITED STATES PATENT AND TRADEMARK OFFICE
CERTIFICATE OF CORRECTION

PATENT NO. : 5,611,778
DATED : March 18, 1997
INVENTOR(S) : Thierry Brinon

It is certified that error appears in the above-indentified patent and that said Letters Patent is hereby corrected as shown below:

On the title page:

Item [22] PCT Filed: Replace "May 12, 1993" with
--May 13, 1993--.

Signed and Sealed this

Twenty-first Day of October 1997

Attest:

BRUCE LEHMAN

Attesting Officer   Commissioner of Patents and Trademarks